(12) United States Patent
Zhang et al.

(10) Patent No.: US 8,993,575 B2
(45) Date of Patent: Mar. 31, 2015

(54) [1,3,4] OXADIAZOLE DERIVATIVE AND APPLICATION THEREOF

(75) Inventors: Guisen Zhang, Xuzhou (CN); Yin Chen, Xuzhou (CN); Xiangqing Xu, Xuzhou (CN); Bifeng Liu, Wuhan (CN); Xiaojun Feng, Wuhan (CN); Song Zhao, Xuzhou (CN); Shicheng Liu, Xuzhou (CN); Minquan Yu, Xuzhou (CN); Yu Lan, Wuhan (CN); Yinli Qiu, Xuzhou (CN)

(73) Assignees: Huazhong University of Science & Technology, Hubei (CN); NHWA Pharma Corporation, Jiangsu (CN)

( * ) Notice: Subject to any disclaimer, the term of this patent is extended or adjusted under 35 U.S.C. 154(b) by 0 days.

(21) Appl. No.: 14/008,693

(22) PCT Filed: Apr. 1, 2012

(86) PCT No.: PCT/CN2012/073470
§ 371 (c)(1),
(2), (4) Date: Sep. 30, 2013

(87) PCT Pub. No.: WO2012/130183
PCT Pub. Date: Oct. 4, 2012

(65) Prior Publication Data
US 2014/0024656 A1    Jan. 23, 2014

(30) Foreign Application Priority Data
Apr. 1, 2011   (CN) .......................... 2011 1 0082555

(51) Int. Cl.
    A61K 31/496    (2006.01)
    A61K 31/454    (2006.01)
    A61K 31/4545   (2006.01)
    C07D 413/14    (2006.01)
    C07D 417/12    (2006.01)
    C07D 417/14    (2006.01)

(52) U.S. Cl.
    CPC ............ *C07D 417/12* (2013.01); *C07D 413/14* (2013.01); *C07D 417/14* (2013.01)
    USPC .................. 514/253.1; 514/254.03; 514/318; 514/321; 544/364; 544/368; 546/194; 546/198

(58) Field of Classification Search
    None
    See application file for complete search history.

(56) References Cited

PUBLICATIONS

Yagcioglu, Turkish Journal of Psychiatry, vol. 18(4), p. 1-10 (2007).*
English abstract for CN102180872 (Sep. 14, 2011).*

* cited by examiner

*Primary Examiner* — Emily Bernhardt
(74) *Attorney, Agent, or Firm* — Prakash Subbiah; Pearl Cohen Zedek Latzer Baratz LLP

(57) ABSTRACT

The present invention belongs to the medicinal chemistry field, and specifically discloses a [1,3,4]oxadiazole derivative with the structure of general formula (I) and pharmaceutically acceptable salt thereof. The compound can be used to prepare a medicine for preventing or treating a disease of the central nervous system.

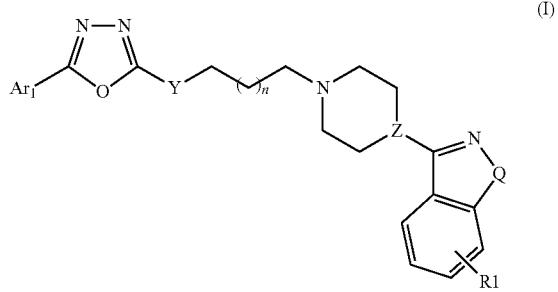

15 Claims, No Drawings

[1,3,4] OXADIAZOLE DERIVATIVE AND APPLICATION THEREOF

CROSS-REFERENCE TO RELATED APPLICATIONS

This application is a National Phase Application of PCT International Application No. PCT/CN2012/073470, International Filing Date Apr. 1, 3012, claiming priority of Chines Patent Applications, 201110082555.1, filed Apr. 1, 2011, all of which are incorporated herein by reference in their entirety.

TECHNICAL FIELD

The invention relates to the medicinal chemistry field. In particular, the invention relates to a novel [1,3,4]oxadiazole derivate, the preparing method thereof and the use thereof for the treatment of psychoneurosis.

BACKGROUND

Schizophrenia is a type of disease characterized in severely schizophrenic cognition and emotion, presenting as the influence on the basic behavior of a human, such as language, thinking, feeling, self-perception or the like. This disease encompasses a large variety of disorders, such as those involved in psyche, e.g. delusion, paranoia, illusion or the like. About 1% of the people all over the world suffer from schizophrenia, and only 5% of them can be cured after treatments. Typical anti-psychosis drug (e.g. chlorpromazine, haloperidol) blocks the dopamine $D_2$ receptor, and severe blocking of dopamine receptor leads to extrapyramidal system (EPS) side effects, including tardive dyskinesia and increased prolactin secretion. In addition, the typical anti-schizophrenia drug is not effective for negative symptoms.

Unlike the typical anti-psychosis drug, the "non-typical" anti-psychosis drug, such as clozapine and risperidone, has low possibility of extrapyramidal system (EPS) side effects and tardive dyskinesia side effects etc. Moreover, it can effectively improve negative symptoms and cognitive disorders. However, these drugs have the side effects of extended QT interval, hyperprolactinemia, weight gain or the like. Therefore, it is important to find new anti-psychosis drug, which is effective for schizophrenia and has fewer side effect.

Through the analysis of the drugs in the market and the compounds under development, it has been found that five receptors are important for schizophrenia, i.e. $D_2$, $D_3$, 5-$HT_{1A}$, 5-$HT_{2A}$ and 5-$HT_{2C}$. The distribution of $D_3$ receptor in brain mainly locates specifically at limbic system, and this system is closely related with human psychic activity. The gene variation frequency of $D_3$ receptor in a patient with schizophrenia is significantly higher than that in control population, which is also closely related with the response to drug therapy. There are two major DA neural pathways for $D_3$ receptor in brain: one is nigrostriatal pathway regulating the motion function, while the other is mesencephalic ventral tegmental area-accumbens nucleus-prefrontal cortex DA pathway closely associated with learning cognition and emotion behavior, of which the disorder will lead to schizophrenia. This DA pathway is the main pathway of reward effect in brain. $D_3$ receptor is distributed in both of the DA neural pathways, and has complex interactions with other DA receptor subtypes, and thus may be the target of anti-psychosis drug therapy. Selective $D_3$ receptor antagonism can reduce the negative and cognitive symptoms of schizophrenia, which additionally can prevent extrapyramidal system side effects, including tardive dyskinesia, Parkinson's disease or the like.

5-hydroxy tryptamine system plays an important role in modulating the function of prefrontal cortex (PFC), including emotion control, cognitive behavior and working memory. The pyramidal neurons and GABA interneurons of PFC contain several 5-hydroxy tryptamine receptor subtypes 5-$HT_{1A}$ and 5-$HT_{2A}$ in high density. It has been shown recently that PFC and NMDA receptor channels are the targets of 5-$HT_{1A}$ receptor, and these two receptors modulate the excitatory neuron of cerebral cortex, thereby affecting the cognitive function. In fact, various preclinical data have shown that 5-$HT_{1A}$ receptor may be the new target of the development of anti-psychosis drug. The 5-$HT_{1A}$ receptor affinity has contributed to non-typical anti-psychosis drug (e.g. olanzapine, aripiprazole or the like) and its low EPS side effects in clinical efficacy. It has been shown recently that 5-$HT_{1A}$ agonist is associated with non-typical anti-psychosis drug therapy, which can improve negative symptoms and cognitive disorders. In the treatment of schizophrenia with the non-typical anti-psychosis drug clozapine, it was found that 5-$HT_{2A}$ plays an important role in various aspects, including cognition, emotion regulation and motion control. The blocking of 5-$HT_{2A}$ receptor can normalize the release of dopamine, exerting the effect of anti-psychosis. In addition, 5-$HT_{2C}$ receptor is closely related with weight gain.

Therefore, it is needed to find novel drugs, which can extend the anti-schizophrenia scope in the manner of multiple receptor binding and has less side effects.

SUMMARY

It is the object of the invention to provide a novel [1,3,4] oxadiazole derivate with pharmaceutical activity based on the prior art.

It is another object of the invention to provide a pharmaceutical composition comprising the above mentioned compound.

It is another object of the invention to provide a method for treating or preventing central nervous system disease, comprising administrating the [1,3,4]oxadiazole derivate according to the invention to the patient in need thereof.

It is another object of the invention to provide use of the above mentioned compound in the treatment or prevention of central nervous system disease.

The objects of the invention can be achieved by the following solutions.

A [1,3,4]oxadiazole derivate having the general formula (I) or a pharmaceutically acceptable salt thereof,

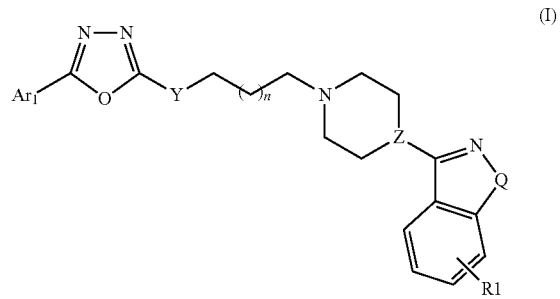

wherein,
Q is O, S or N;
Y is O or S;
Z is N or CH;
n is 1, 2 or 3;

R1 is H, halogen, cyano, $C_{1-5}$alkoxy, $C_{1-5}$alkyl, said $C_{1-5}$alkyl being unsubstituted or substituted by one or more substituents selected from the group consisting of amino, hydroxyl and halogen;

$Ar_1$ is the group of formula (II), formula (III) or formula (IV),

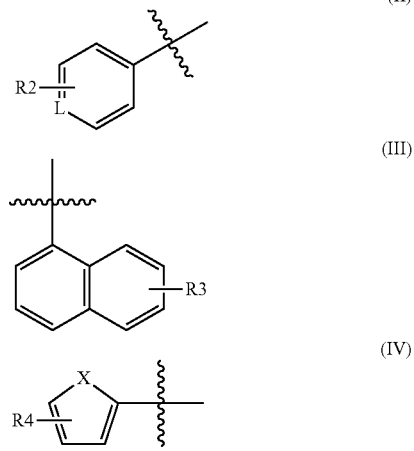

L is CH or N;

X is O, NH, S or $CH_2$;

R2, R3 and R4 are each independently H, halogen, cyano, aromatic ring, hydroxyl, $C_{1-5}$alkoxy, $C_{1-5}$alkyl, said $C_{1-5}$alkyl being unsubstituted or substituted by one or more substituents selected from the group consisting of amino, hydroxyl and halogen (such as F).

Preferably, in the compound of formula (I), R1, R2, R3 and R4 are each independently H, halogen, $C_{1-5}$alkoxy, $C_{1-5}$alkyl or fluorinated $C_{1-5}$alkyl. More preferably, R1 is H or halogen, and R2, R3 and R4 are each independently H, methoxy, Cl, F or trifluoromethyl. Most preferably, R1 is at 6-position. Most preferably, R2 is at 4-position.

Preferably, in the compound of formula (I), Q is O or S; Y is S; n is 1; X is S.

When $Ar_1$ is the group of formula (II), preferably, R1 and R2 are each independently selected from the group consisting of H, halogen, cyano, aromatic ring, hydroxyl, $C_{1-5}$alkyl, fluorinated $C_{1-5}$alkyl or $C_{1-5}$alkoxy; L is selected from the group consisting of CH or N; Q is selected from group consisting of O, S and N; Z is N or CH; n is 1, 2 or 3; Y is selected from group consisting of O or S. When $Ar_1$ is the group of formula (II), more preferably, Q is O or S; Y is S; Z is N or CH; n is 1; L is CH or N; R1 and R2 are each independently H, methoxy, Cl, F or trifluoromethyl. When $Ar_1$ is the group of formula (III), preferably, R1 and R3 are each independently selected from the group consisting of H, halogen, cyano, aromatic ring, hydroxyl, $C_{1-5}$alkyl, $C_{1-5}$alkoxy; Q is selected from the group consisting of O, S or N; Z is selected from the group consisting of N or CH; n is an integer of 1-3; Y is O or S. When $Ar_1$ is the group of formula (III), more preferably, Q is O or S; Y is S; Z is N or CH; n is 1; R1 and R3 are each independently H or F.

When $Ar_1$ is the group of formula (IV), preferably, R1 and R4 are each independently selected from the group consisting of H, halogen, cyano, aromatic ring, hydroxyl, $C_{1-5}$alkyl, $C_{1-5}$alkoxy; X is selected from the group consisting of O, NH, S or $CH_2$; Z is selected from the group consisting of N or CH; n is an integer of 1-3; Y is O or S. When $Ar_1$ is the group of formula (IV), more preferably, Q is O or S; Y is S; Z is N or CH; n is 1; R1 and R4 are each independently selected from the group consisting of H or F.

In the compound of formula (I), when Q is O, then Z is preferably CH; when Q is S, then Z is preferably N.

In another preferable embodiment of the compound of formula (I):

When $Ar_1$ is the group of formula (II), then R1 is H or F; Y is S; n is 1; Q is S or O; Z is N or CH; L is CH or N; R2 is H, methoxy, Cl, trifluoromethyl or F. More preferably, when R1 is H, then Y is S; n is 1; Q is S; Z is N; L is CH; R2 is H, methoxy, Cl, trifluoromethyl or F; when R1 is F, then Y is S; n is 1; Q is O; Z is CH; L is CH; R2 is H, methoxy, Cl, trifluoromethyl or F; when R1 and R2 are both H, then Y is S; n is 1; Q is S; Z is N; L is N; or when R1 is F, then Y is S; n is 1; Q is O; Z is CH; L is N.

When $Ar_1$ is the group of formula (III), then R1 is H or F; Y is S; n is 1; Q is S or O; Z is N or CH; R3 is H. More preferably, when R1 is H, then Y is S; n is 1; Q is S; Z is N; R3 is H; or when R1 is F, then Y is S; n is 1; Q is O; Z is CH; R3 is H.

When $Ar_1$ is the group of formula (IV), then R1 is H or F; Y is S; n is 1; Q is S or O; Z is N or CH; X is S. More preferably, when R1 is H, then Y is S; n is 1; Q is S; Z is N; X is S; or when R1 is F, then Y is S; n is 1; Q is O; Z is CH; X is S.

Most preferably, the compounds of formula (I) according to the invention are selected from the group consisting of the following compounds or the pharmaceutically acceptable salts thereof:

2-((3-(4-(3-benzisothiazole)-1-piperazinyl)propylthio)-5-phenyl-1,3,4-oxadiazole;

2-((3-(4-(3-(6-fluoro-benzisoxazole))-1-piperidyl)propylthio)-5-phenyl-1,3,4-oxadiazole;

2-((3-(4-(3-benzisothiazole)-1-piperazinyl)propylthio)-5-(4-methoxyphenyl)-1,3,4-oxadiazole;

2-((3-(4-(3-(6-fluoro-benzisoxazole))-1-piperidyl)propylthio)-5-(4-methoxyphenyl)-1,3,4-oxadiazole;

2-((3-(4-(3-benzisothiazole)-1-piperazinyl)propylthio)-5-(4-chlorophenyl)-1,3,4-oxadiazole;

2-((3-(4-(3-(6-fluoro-benzisoxazole))-1-piperidyl)propylthio)-5-(4-chlorophenyl)-1,3,4-oxadiazole;

2-((3-(4-(3-benzisothiazole)-1-piperazinyl)propylthio)-5-(4-trifluoromethyl)phenyl)-1,3,4-oxadiazole;

2-((3-(4-(3-(6-fluoro-benzisoxazole))-1-piperidyl)propylthio)-5-(4-trifluoromethyl)phenyl)-1,3,4-oxadiazole;

2-((3-(4-(3-benzisothiazole)-1-piperazinyl)propylthio)-5-(4-fluoro)phenyl)-1,3,4-oxadiazole;

2-((3-(4-(3-(6-fluoro-benzisoxazole))-1-piperidyl)propylthio)-5-(4-fluoro)phenyl)-1,3,4-oxadiazole;

2-((3-(4-(3-benzisothiazole)-1-piperazinyl)propylthio)-5-(1-naphthyl)-1,3,4-oxadiazole;

2-((3-(4-(3-(6-fluoro-benzisoxazole))-1-piperidyl)propylthio)-5-(1-naphthyl)-1,3,4-oxadiazole;

2-((3-(4-(3-benzisothiazole)-1-piperazinyl)propylthio)-5-(2-thienyl)-1,3,4-oxadiazole;

2-((3-(4-(3-(6-fluoro-benzisoxazole))-1-piperidyl)propylthio)-5-(2-thienyl)-1,3,4-oxadiazole;

2-((3-(4-(3-benzisothiazole)-1-piperazinyl)propylthio)-5-(4-pyridyl)-1,3,4-oxadiazole; and 2-((3-(4-(3-(6-fluoro-benzisoxazole))-1-piperidyl)propylthio)-5-(4-pyridyl)-1,3,4-oxadiazole.

DETAILED DESCRIPTION OF THE INVENTION

For the purpose of the invention, the term "$C_{1-5}$alkyl" refers to a linear or branched alkyl containing 1, 2, 3, 4, or 5 carbon atoms. For example, a $C_{1-5}$alkyl may be methyl, ethyl, n-propyl, isopropyl, n-butyl, isobutyl, t-butyl, n-pentyl, isopentyl, neopentyl or the like. The term "$C_{1-5}$alkoxy" refers to the above-defined $C_{1-5}$alkyl, which is attached to the rest of the molecule via an oxygen atom.

The term "unsubstituted or substituted" means the group defined with this term may be unsubstituted or substituted by one or more designated substituents.

The term "aromatic ring" refers to an aromatic ring group having 5-14 carbon ring atoms, preferably 5-10 or 6-10 carbon ring atoms, for example, phenyl or naphthyl. Any aryl defined herein may be substituted by one, two or more substituents preferably selected from the group consisting of halogen, hydroxyl, cyano, amino, $C_{1-5}$alkyl (e.g. methyl or ethyl) and $C_1$-$C_5$alkoxy (e.g. methoxy).

The term "halogen" refers to F (fluorine), Cl (chlorine), Br (bromine) or I (iodine).

In addition, the invention provides use of the compounds according to the invention and the pharmaceutical composition consisting of such compounds in the manufacture of a medicament for the treatment or prevention of central nervous system disorders selected from the group consisting of mental disorder, anxiety, personality disorder, depression, mania, migraine, epilepsy or spasticity disorder, childhood disorder, Parkinson's disease, cognitive disorder, neural degeneration, neurotoxicity and ischemia, preferably schizophrenia Furthermore, the invention provides a pharmaceutical composition, comprising the compound of formula (I) or the pharmaceutically acceptable salt thereof, and pharmaceutically acceptable adjuvant (e.g. carrier and/or excipient). The pharmaceutical composition is a anti-psychosis composition comprising the compound according to the invention in an amount sufficient to exert anti-psychosis effect.

The effective dose of the present compounds can be orally administrated with, for example, inert diluent or some carriers. It can be encapsulated in a gelatin capsule or compressed into a tablet. For the purpose of oral treatment, the compounds according to the invention can be used with excipients and in the forms of tablet, troche, capsule, suspension, syrup or the like. These formulation should contain the active compounds according to the invention in an amount of at least 0.5 wt %, but such an amount can vary according to particular formulations, and the amount of 4-70% by weight will be beneficial. The active compounds should be present in a suitable dosage in such compositions. The oral unit dose of the preferable composition and formulation according to the invention contains 1.0-300 mg of the active compounds according to the invention.

The compound provided herein, i.e. the compound of formula (I) and the pharmaceutically acceptable salt, solvate and hydrate thereof can be combined with pharmaceutically acceptable carrier or diluent to form a pharmaceutical formulation. The pharmaceutically acceptable carrier comprises inert solid filler or diluent and sterile aqueous solution or organic solution.

The dosage of the compound according to the invention depends on the type and severity of the disease or disorder, and the nature of the subject, for example, general health, age, gender, weight and drug tolerance. A person skilled in the art can determine the suitable dosage according to these or other factors. Generally, the effective dosage for a central nervous system drug is well known to a person skilled in the art. The total daily dosage is generally about 0.05 mg-2000 mg.

The invention relates to a pharmaceutical composition, which can provide about 0.01-1000 mg active ingredient per unit dose. The composition can be administrated in any suitable route, for example, oral administration in a capsule, parenteral administration in an injection, topical administration in an ointment or a lotion, rectal administration in a suppository, or transdermal administration in a patch.

The compounds according to the invention can be combined with suitable solid or liquid carrier or diluent to form capsule, tablet, pill, powder, syrup, solution or the like. The tablet, pill, capsule or the like contains about 0.01% to about 99% by weight of active ingredients, and binder, such as gelatin, maize starch, arabic gum etc; excipient, such as calcium hydrophosphate; disintegrant, such as maize starch, potato starch or alginic acid; lubricant, such as magnesium stearate; and sweetener, such as sucrose, lactose. When the formulation is in the form of capsule, in addition to above materials, it may also contain liquid carrier, for example, grease.

For the parenteral administration, the compounds according to the invention can be combined with sterile water or organic medium to form injectable solution or suspension.

The compounds according to the invention may contain a chiral center(s), thereby be present in the forms of different enantiomers or diastereomers. Accordingly, the invention relates to all the optical isomers and all the stereoisomers of the present compounds, in the forms of racemic mixture and respective enantiomers and diastereomers. Moreover, the invention relates to the above defined compounds or all the pharmaceutical compositions containing or using the same as well as the therapeutical method using the same.

The compound of general formula (I) can form a pharmaceutically acceptable salt with an acid. The pharmaceutically acceptable salt may be hydrochloride, hydrobromide, hydriodate, nitrate, sulfate or bisulfate, phosphate or acid phosphate, acetate, lactate, citrate, tartrate, maleate, fumarate, mesylate, gluconate, saccharate, benzoate, ethanesulfonate, benzenesulfonate, p-toluenesulfonate or the like.

General Synthesis Scheme

The Examples of the invention react substituted carboxylic acid with ethanol to form ester in the presence of concentrated sulfuric acid; the ester is hydrazinolyzed with hydrazine hydrate to form corresponding acylhydrazine, which is cyclized with carbon disulfide in the presence of potassium hydroxide and anhydrous ethanol to give 1,3,4-oxadizzole; the 1,3,4-oxaciazole is then reacted with 1,3-dibromopropane (or 1,4-dibromobutane, 1,5-dibromopentane) in the presence of potassium carbonate or potassium hydroxide as acid-binding reagent to give bromide; and the bromide is reacted with corresponding substituted piperazine or piperidine to give the target product.

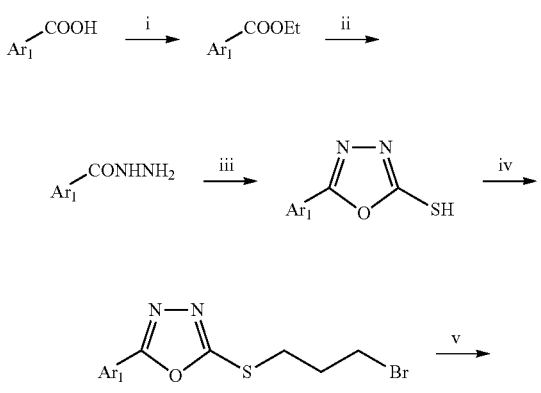

-continued

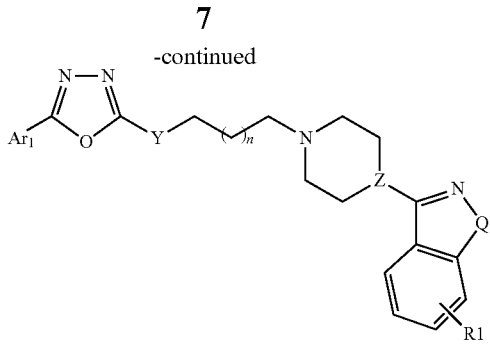

Reaction conditions: (i) ethanol, concentrated sulfuric acid; (ii) 80% hydrazine hydrate; (iii) carbon disulfide, potassium hydroxide; (iv) 1,3-dibromopropane, potassium hydroxide; (v) aryl piperazine, anhydrouse potassium carbonate.

It is shown in the in vitro receptor binding assay that the compounds according to the invention have relatively higher affinities for dopamine $D_2$, $D_3$, $5\text{-}HT_{1A}$ and $5\text{-}HT_{2A}$ receptors, while lower affinities for $5\text{-}HT_{2C}$ (reduce the risk of obesity under long term therapy) so as to increase the efficacy of the drug (e.g. improve the negative symptoms) and reduce the side effects (e.g. EPS, increased prolactin, weight gain and extended QI interval).

It is shown in the animal experiment that these compounds can significantly improve the MK-801 induced high activity and effectively improve the apomorphine induced clambering symptoms without causing EPS at effective dosage, indicating that they have significant anti-schizophrenia effect. Since these in vitro acting targets and in vivo pharmacological models are closely associated with dopamine function disorder induced neural system disease, particularly schizophrenia, it is indicated that the compounds according to the invention have the therapeutic effect for neuropsychical diseases, especially schizophrenia. The detailed pharmacological data of each of the compounds are listed in Table 1.

EXAMPLE

The following Examples are provided for illustrative purposes rather than limiting to the invention. Otherwise indicated, all the temperatures are shown as Celsius (° C.).

Example 1

2-((3-(4-(3-benzisothiazole)-1-piperazinyl)propylthio)-5-phenyl-1,3,4-oxadiazole 1) To a flask were added 6.1 g of benzoic acid and 40 ml of anhydrous ethanol, to which 2 ml of concentrated sulfuric acid was added slowly and dropwise with stirring, and the mixture was heated under reflux for 6 hours, and then cooled to room temperature. The solvent was distilled under reduced pressure, and the residue was diluted with 30 ml of ethyl acetate and 25 ml of water. The aqueous layer was extracted with ethyl acetate (30 ml×2) and the organic layers were combined, washed with saturated sodium bicarbonate solution to neutral and then with saturated NaCl, dried with anhydrous magnesium sulfate, and filtrated. The solvent was distilled under reduced pressure to give ethyl benzoate.

2) To a 100 ml 3-neck flask were added 40 ml of ethanol and 6 g of ethyl benzoate, to which 12.5 g of 85% hydrazine hydrate was added slowly and dropwise with stirring. After the addition was completed, the mixture was heated under reflux for 8 hours and then cooled to room temperature. The solvent was distilled under reduced pressure and water was added. The solid was precipitated. The mixture was allowed to stand for 30 min until the solid was fully precipitated, which was filtrated and washed with water. Recrystallization with anhydrous ethanol gave benzoyl hydrazine.

3) To a 100 ml flask were added 2.7 g of benzoyl hydrazine, a solution of 1.2 g potassium hydroxide in ethanol (20 ml) and 3 g of carbon disulfide. The mixture was heated under reflux for 6 hours with stirring. The solvent was distilled under reduced pressure and water was added to dissolve the solid. The pH was adjusted to 6-7 with 10% hydrochloric acid and a lot of solid was precipitated, which was filtrated, and recrystallized with anhydrous ethanol to give 5-phenyl-2-mercapto-1,3,4-oxadiazole. MP: 212-214° C.

4) 5-phenyl-2-mercapto-1,3,4-oxadiazole, potassium hydroxide, acetonitrile and 1,3-dibromopropane were heated under reflux for 1 hour, and then cooled to room temperature. The reaction mixture was filtrated, and the solvent was removed by rotation to give yellowish oil, which was passed through a column to give white solid. Melting point: 61-63° C.

5) To the product of step 4) were added 3-(1-piperazinyl)-1,2-benzisothiazole hydrochloride, anhydrous potassium carbonate, potassium iodide and acetonitrile, and the mixture was heated under reflux for 24 hours, and then cooled to room temperature and filtrated. The solvent was distilled to give yellowish oil, which was passed through a column to give white solid.

$^1$H NMR (CDCl$_3$) δ 2.11-2.14 (m, 2H), 2.64 (t, 2H, J=13.6 Hz), 2.72-2.74 (m, 4H), 3.40 (t, 2H, J=14 Hz), 3.58-3.60 (m, 4H), 7.33-7.37 (m, 1H), 7.44-7.52 (m, 4H), 7.80 (d, 1H, J=8 Hz), 7.89 (d, 1H, J=8.4 Hz), 7.99 (d, 1H, J=2 Hz)

MS (ESI) m/z 438.2 ([M+H]$^+$).

Example 2

2-((3-(4-(3-(6-fluoro-benzisoxazole))-1-piperidyl)propylthio)-5-phenyl-1,3,4-oxadiazole 1) To a flask were added 6.1 g of benzoic acid and 40 ml of anhydrous ethanol, to which 2 ml of concentrated sulfuric acid was added slowly and dropwise with stirring. The mixture was heated under reflux for 6 hours, and then cooled to room temperature. The solvent was distilled under reduced pressure and the residue was diluted with 30 ml of ethyl acetate and 25 ml of water. The aqueous layer was extracted with ethyl acetate (30 ml×2) and the organic layers were combined, washed with saturated sodium bicarbonate solution to neutral and then with saturated NaCl, dried with anhydrous magnesium sulfate, and filtrated. The solvent was distilled under reduced pressure to give ethyl benzoate.

2) To a 100 ml 3-neck flask were added 40 ml of ethanol and 6 g of ethyl benzoate, to which 12.5 g of 85% hydrazine hydrate was added slowly and dropwise with stirring. After the addition was completed, the reaction mixture was heated under reflux for 8 hours and then cooled to room temperature. The solvent was distilled under reduced pressure and water was added. The solid was precipitated. The mixture was allowed to stand for 30 min until the solid was fully precipitated, which was filtrated and washed with water. Recrystallization with anhydrous ethanol gave benzoyl hydrazine.

3) To a 100 ml flask were added 2.7 g of benzoyl hydrazine, a solution of 1.2 g potassium hydroxide in ethanol (20 ml) and 3 g of carbon disulfide. The mixture was heated under reflux for 6 hours with stirring. After the reaction was completed, the solvent was distilled under reduced pressure and water was added to dissolve the solid. The pH was adjusted to 6-7 with 10% hydrochloric acid and a lot of solid was precipitated, which was filtrated, and recrystallized with anhydrous ethanol to give 5-phenyl-2-mercapto-1,3,4-oxadiazole. MP: 212-214° C.

4) 5-phenyl-2-mercapto-1,3,4-oxadiazole, potassium hydroxide, acetonitrile and 1,3-dibromopropane were heated under reflux for 1 hour, and then cooled to room temperature. The mixture was filtrated, and the solvent was removed by rotation to give yellowish oil, which was passed through a column to give white solid. Melting point: 61-63° C.

5) To the product of step 4) were added 6-fluoro-3-(4-piperidyl)-1,2-benzisoxazole hydrochloride, anhydrous potassium carbonate, potassium iodide and acetonitrile, and the mixture was heated under reflux for 24 hours, then cooled to room temperature and filtrated. The solvent was distilled to give yellowish oil, which was passed through a column to give white solid.

$^1$H NMR (CDCl$_3$) δ 2.05-2.18 (m, 8H), 2.57 (t, 2H, J=13.6H), 3.05-3.09 (m, 4H), 3.40 (t, 2HH, J=14.4 Hz), 7.05 (m, 1H), 7.24 (dd, 1H, J1=2 Hz, J2=2 Hz), 7.49-7.51 (m, 3H), 7.68-7.71 (m, 1H), 7.99-8.02 (m, 2H)

MS (ESI) m/z 439.2 ([M+H]$^+$).

Example 3

2-((3-(4-(3-benzisothiazole)-1-piperazinyl)propylthio)-5-(4-methoxyphenyl)-1,3,4-oxadiazole The target compound was obtained according to the procedures of Example 1, using p-methoxybenzoic acid as starting material.

$^1$H NMR (CDCl$_3$) δ 2.08-2.11 (m, 2H), 2.61 (t, 2H, J=13.6 Hz), 2.69 (t, 4H, J=9.6 Hz), 3.38 (t, 2H, J=14.4 Hz), 3.57 (t, 4H, J=9.6 Hz), 3.87 (s, 3H), 6.99 (d, 2H, J=8.8 Hz), 7.35 (t, 1H), 7.46 (t, 1H), 7.80 (d, 1H, J=8.4 Hz), 7.89-7.95 (m, 3H)

MS (ESI) m/z 468.2 ([M+H]$^+$).

Example 4

2-((3-(4-(3-(6-fluoro-benzisoxazole))-1-piperidyl)propylthio)-5-(4-methoxyphenyl)-1,3,4-oxadiazole The target compound was obtained according to the procedures of Example 2, using p-methoxybenzoic acid as starting material.

$^1$H NMR (CDCl$_3$) δ 2.04-2.17 (m, 8H), 2.57 (t, 2H, J=13.6 Hz), 3.04-3.08 (m, 3H), 3.37 (t, 2H, J=14 Hz), 3.86 (s, 3H), 6.99-7.07 (m, 3H), 7.21-7.30 (m, 1H), 7.68-7.71 (m, 1H), 7.91-7.95 (m, 2H), 7.80 (d, 1H, J=8.4 Hz), 7.89-7.95 (m, 3H)

MS (ESI) m/z 469.2 ([M+H]$^+$).

Example 5

2-((3-(4-(3-benzisothiazole)-1-piperazinyl)propylthio)-5-(4-chlorophenyl)-1,3,4-oxadiazole The target compound was obtained according to the procedures of Example 1, using p-chlorobenzoic acid as starting material.

$^1$H NMR (CDCl$_3$) δ 2.08-2.12 (m, 2H), 2.59-2.67 (m, 6H), 3.07, (br, 4H), 3.42 (t, 2H, J=14.4 Hz), 6.93-6.96 (m, 1H), 7.15 (m, 2H), 7.77 (d, 2H, J=8 Hz), 8.14 (d, 2H, J=8.4 Hz)

MS (ESI) m/z 472.2 ([M+H]$^+$).

Example 6

2-((3-(4-(3-(6-fluoro-benzisoxazole))-1-piperidyl)propylthio)-5-(4-chlorophenyl)-1,3,4-oxadiazole The target compound was obtained according to the procedures of Example 2, using p-chlorobenzoic acid as starting material.

$^1$H NMR (CDCl$_3$) δ 2.08-2.20 (m, 8H), 2.58 (m, 2H), 3.06-3.09 (m, 3H), 3.40 (t, 2H, J=14.4 Hz), 7.06 (m, 1H), 7.46-7.48 (m, 2H), 7.68-7.72 (m, 1H), 7.94-7.96 (m, 2H)

MS (ESI) m/z 473.2 ([M+H]$^+$).

Example 7

2-((3-(4-(3-benzisothiazole)-1-piperazinyl)propylthio)-5-(4-trifluoromethyl)phenyl)-1,3,4-oxadiazole The target compound was obtained according to the procedures of Example 1, using p-trifluoromethylbenzoic acid as starting material.

$^1$H NMR (CDCl$_3$) δ 2.10-2.14 (m, 2H), 2.60-2.71 (m, 6H), 3.43 (t, 2H, J=14 Hz), 3.58 (br, 4H), 7.33-7.37 (m, 1H), 7.44-7.48 (m, 1H), 7.75-7.82 (m, 3H), 7.90 (d, 1H, J=8 Hz), 8.13 (d, 2H, J=8 Hz)

MS (ESI) m/z 506.2 ([M+H]$^+$).

Example 8

2-((3-(4-(3-(6-fluoro-benzisoxazole))-1-piperidyl)propylthio)-5-(4-trifluoromethyl)phenyl)-1,3,4-oxadiazole The target compound was obtained according to the procedures of Example 2, using p-trifluoromethylbenzoic acid as starting material.

$^1$H NMR (CDCl$_3$) δ 2.08-2.19 (m, 8H), 2.59 (t, 2H J=13.6 Hz), 3.06-3.12 (m, 3H), 3.43 (t, 2H, J=14 Hz), 7.06-7.08 (m, 1H), 7.23-7.27 (m, 2H), 7.68-7.72 (m, 1H), 7.77 (d, 2H, J=8.4 Hz), 8.14 (d, 1H, J=8 Hz)

MS (ESI) m/z 507.2 ([M+H]$^+$).

Example 9

2-((3-(4-(3-benzisothiazole)-1-piperazinyl)propylthio)-5-(4-fluoro)phenyl)-1,3,4-oxadiazole The target compound was obtained according to the procedures of Example 1, using p-fluorobenzoic acid as starting material.

$^1$H NMR (CDCl$_3$) δ2.06-2.10 (m, 2H), 2.57-2.68 (m, 6H), 3.38 (t, 2H, J=14 Hz), 3.53-3.56 (m, 4H), 7.13-7.17 (m, 2H), 7.32-7.43 (m, 2H), 7.77-7.99 (m, 4H)

MS (ESI) m/z 457.2 ([M+H]$^+$).

Example 10

2-((3-(4-(3-(6-fluoro-benzisoxazole))-1-piperidyl)propylthio)-5-(4-fluoro)phenyl)-1,3,4-oxadiazole The target compound was obtained according to the procedures of Example 2, using p-fluorobenzoic acid as starting material.

¹H NMR (CDCl₃) δ2.05-2.17 (m, 8H), 2.57 (t, 2H, J=13.6 Hz), 3.05-3.07 (m, 3H), 3.40 (t, 2H, J=14 Hz), 7.05-7.06 (m, 1H), 7.16-7.25 (m, 3H), 7.68-7.71 (m, 1H), 8.00-8.03 (m, 2H)
MS (ESI) m/z 456.2 ([M+H]⁺).

Example 11

2-((3-(4-(3-benzisothiazole)-1-piperazinyl)propylthio)-5-(1-naphthyl)-1,3,4-oxadiazole The target compound was obtained according to the procedures of Example 1, using 1-naphthoic acid as starting material.
¹H NMR (CDCl₃) δ2.11-2.18 (m, 2H), 2.62-2.72 (m, 6H), 3.44 (t, 2H, J=14 Hz), 3.56-3.59 (m, 4H), 7.32-8.13 (m, 10H), 9.21 (d, 1H, J=8.8 Hz)
MS (ESI) m/z 488.3 ([M+H]⁺).

Example 12

2-((3-(4-(3-(6-fluoro-benzisoxazole))-1-piperidyl)propylthio)-5-(1-naphthyl)-1,3,4-oxadiazole The target compound was obtained according to the procedures of Example 2, using 1-naphthoic acid as starting material.
¹H NMR (CDCl₃) δ2.06-2.16 (m, 8H), 2.60 (t, 2H, J=6.8 Hz), 3.07-3.10 (m, 3H), 3.45 (t, 2H, J=14 Hz), 7.05 (m, 1H), 7.23-7.26 (m, 1H), 7.56-7.59 (m, 2H), 7.67-7.69 (m, 2H), 7.92 (d, 1H, J=8.4 Hz), 8.13 (d, 1H, J=7.2 Hz), 9.21 (d, 1H, J=8.8 Hz)
MS (ESI) m/z 489.3 ([M+H]⁺).

Example 13

2-((3-(4-(3-benzisothiazole)-1-piperazinyl)propylthio)-5-(2-thienyl)-1,3,4-oxadiazole The target compound was obtained according to the procedures of Example 1, using thiophene-2-carboxylic acid as starting material.
¹H NMR (CDCl₃) δ2.07-2.11 (m, 2H), 2.60 (t, 2H, J=13.6 Hz), 2.68-2.70 (m, 4H), 3.38 (t, 2H, J=14 Hz), 3.55-3.58 (m, 4H), 7.13-7.15 (m, 1H), 7.35 (t, 1H, J=15.2 Hz), 7.51-7.53 (m, 1H), 7.69-7.70 (m, 1H), 7.80 (d, 1H, J=8 Hz), 7.90 (d, 1H, J=8.4 Hz)
MS (ESI) m/z 444.2 ([M+H]⁺).

Example 14

2-((3-(4-(3-(6-fluoro-benzisoxazole))-1-piperidyl)propylthio)-5-(2-thienyl)-1,3,4-oxadiazole The target compound was obtained according to the procedures of Example 2, using thiophene-2-carboxylic acid as starting material.
¹H NMR (CDCl₃) δ2.04-2.17 (m, 8H), 2.56 (t, 2H, J=13.6 Hz), 3.05-3.07 (m, 3H), 3.38 (t, 2H, J=14.4 Hz), 7.05-7.08 (m, 1H), 7.14-7.16 (m, 1H), 7.22-7.25 (m, 1H), 7.52-7.54 (m, 1H), 7.68-7.71 (m, 2H)
MS (ESI) m/z 445.2 ([M+H]⁺).

Example 15

2-((3-(4-(3-benzisothiazole)-1-piperazinyl)propylthio)-5-(4-pyridyl)-1,3,4-oxadiazole The target compound was obtained according to the procedures of Example 1, using 4-picolinic acid as starting material.

¹H NMR (CDCl₃) δ 2.09-2.12 (m, 2H), 2.59-2.67 (m, 6H), 3.10 (br, 4H), 3.44 (t, 2H, J=14 Hz), 3.56 (t, 4H, J=9.6 Hz), 7.33-7.36 (m, 1H), 7.44-7.47 (m, 1H), 7.79-7.91 (m, 3H), 8.78-8.80 (m, 1H)
MS (ESI) m/z 439.2 ([M+H]⁺).

Example 16

2-((3-(4-(3-(6-fluoro-benzisoxazole))-1-piperidyl)propylthio)-5-(4-pyridyl)-1,3,4-oxadiazole The target compound was obtained according to the procedures of Example 2, using 4-picolinic acid as starting material.
MS (ESI) m/z 440.2 ([M+H]⁺).

Example 17

5HT$_{1A}$ Receptor Binding Assay

Preparation of Membrane

Rats were sacrificed by cervical dislocation on ice. Brain mantle was rapidly taken, and 2 brain mantles were combined into a centrifuge tube, to which 3 ml of buffer (0.05 M Tris-HCl buffer, containing 0.1% ascorbic acid, 10 μm pargyline and 4 mM CaCl₂) was added. Homogenization was conducted for 3-4 s at level 4 for four times, and then 5 ml of buffer was added (0.05 M Tris-HCl buffer, containing 0.1% ascorbic acid, 10 μm pargyline and 4 mM CaCl₂). Incubation at 37° C. was conducted for 10 min, the weight of the tubes were adjusted using a balance after incubation. Centrifugation was conducted at 12000 r, 4° C. for 20 min, the supernatant was discarded, and 3 ml of buffer was added (0.05 M Tris-HCl buffer, containing 0.1% ascorbic acid, 10 μm pargyline and 4 mM CaCl₂). Vortex mixer was used for blending, and then 5 ml of buffer was added (0.05 M Tris-HCl buffer, containing 0.1% ascorbic acid, 10 μm pargyline and 4 mM CaCl₂). Centrifugation was conducted and repeated 3 times. After the centrifugations, the supernatant was discarded, and the pellets were stored at −80° C. for future use.

Materials for the Receptor Binding Assay

Isotope ligand ³H-8-OH-DPAT (67.0 Ci/mmol) was purchased from PerkinElmer Company; 5-HT was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of buffer (0.05 M Tris-HCl buffer, containing 0.1% ascorbic acid, 10 μm pargyline and 4 mM CaCl₂), and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer (0.05 M Tris-HCl buffer, containing 0.1% ascorbic acid, 10 μm pargyline and 4 mM CaCl₂) were added into each reaction tube.

(3) 100 μL of homogenized liquid was added into the total binding tube (TB), 100 μL of 5-HT (final concentration 10⁻⁵M) was added into the non-specific binding tube (NB), and 100 μL of the test compound (final concentration 10⁻⁵ M) was added into the specific binding tube (SB) for each compound.

(4) 10 μL of radioactive ligand $^3$H-8-OH-DPAT was respectively added into each reaction tube (2 parallel tubes were used for each reaction tube, and each of them was placed on ice when adding sample).

(5) Each reaction tube was incubated at 37° C. for 10 min; after the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate($I$%)=[(Total binding tube cpm−compound cpm)/(Total binding tube cpm−non-specific binding tube cpm)]×100%

Each assay for the compounds was conducted in duplicate. The results are listed in Table 1.

Example 18

5HT$_{2A}$ Receptor Assay

Preparation of 5HT$_{2A}$ Membrane

Rats were sacrificed by cervical dislocation on ice. Brain mantle was rapidly taken, and 2 brain mantles were combined into a centrifuge tube, to which 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation at 37° C. was conducted for 10 min, the weight of the tubes were adjusted using a balance after incubation. Centrifugation was conducted at 12000 r, 4° C. for 20 min, the supernatant was discarded, and 3 ml of buffer was added (0.05 M Tris-HCl buffer: 6.05 g of Tris was dissolved in 1000 ml of double-distilled water, and concentrated HCl was used to adjust to pH 7.5). Vortex mixer was used for blending, and then 5 ml of buffer was added. Centrifugation was conducted (repeated 3 times). After the centrifugations, the supernatant was discarded, and the pellets were stored at −80° C. for future use.

Materials for the Receptor Binding Assay

Isotope ligand [$^3$H]-Ketanserin (67.0 Ci/mmol) was purchased from PerkinElmer Company; Methysergide was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of buffer (0.05 M Tris-HCl buffer: 6.05 g of Tris was dissolved in 1000 ml of double-distilled water, and concentrated HCl was used to adjust to pH 7.5), and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer (0.05 M Tris-HCl buffer: 6.05 g of Tris was dissolved in 1000 ml of double-distilled water, and concentrated HCl was used to adjust pH 7.5) were added into each reaction tube.

(3) 100 μL of homogenized liquid was added into the total binding tube (TB), 100 μL of MetHysergide (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand $^3$H-Ketanserin was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate($I$%)=[(Total binding tube cpm−compound cpm)/(Total binding tube cpm−non-specific binding tube cpm)]×100%

Each assay for the compounds was conducted in duplicate. The results are listed in Table 1.

Example 19

D$_2$ Receptor Binding Assay

Preparation of Membrane

Rats were sacrificed by cervical dislocation on ice. Brain striatum was rapidly taken, and 2 brain striatums were combined into a centrifuge tube, to which 3 ml of buffer (0.05 M Tris-HCl buffer, containing NaCl 120 mM, KCl 5 mM, MgCl$_2$ 1 mM, CaCl$_2$ 1 mM) was added, homogenization was conducted for 3-4 s at level 4 for four times, and then 5 ml of buffer was then added. The weight of the homogenized tubes were adjusted using a balance, and centrifugation was conducted at 12000 r, 4° C. for 20 min. The supernatant was discarded, and 3 ml of buffer was added (0.05 M Tris-HCl buffer, containing NaCl 120 mM, KCl 5 mM, MgCl$_2$ 1 mM, CaCl$_2$ 1 mM). Vortex mixer was used for blending, and then 5 ml of buffer was added (0.05 M Tris-HCl buffer, containing NaCl 120 mM, KCl 5 mM, MgCl$_2$ 1 mM, CaCl$_2$ 1 mM). Centrifugation was conducted and repeated 3 times. After the centrifugations, the supernatant was discarded, and the pellets were stored at −80° C. for future use.

Materials for the Receptor Binding Assay

Isotope ligand $^3$H-Spiperone (67.0 Ci/mmol) was purchased from PerkinElmer Company; Butaclamol was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of buffer (0.05 M Tris-HCl buffer, containing NaCl 120 mM, KCl 5 mM, MgCl$_2$ 1 mM, CaCl$_2$ 1 mM), and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer (0.05 M Tris-HCl buffer, containing NaCl 120 mM, KCl 5 mM, MgCl$_2$ 1 mM, CaCl$_2$ 1 mM) were added into each reaction tube.

(3) 100 μL of homogenized liquid was added into the total binding tube (TB), 100 μL of Butaclamol (final concentration $10^{-5}$ M) was added into the non-specific binding tube (NB), and 100 µL of the test compound (final concentration $10^{-5}$ M) was added into the specific binding tube (SB) for each compound.

(4) 10 µL of radioactive ligand $^3$H-Spiperone was respectively added into each reaction tube (2 parallel tubes were used for each reaction tube, and each of them was placed on ice when adding sample).

(5) Each of the reaction tubes was incubated at 37° C. for 20 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibitory rate(I%)=[(Total binding tube cpm−compound cpm)/(Total binding tube cpm−non-specific binding tube cpm)]×100%

Each assay for the compounds was conducted in duplicate. The results are listed in Table 1.

Example 20

D$_3$ Receptor Binding Assay

Cells

In HEK-293 cells, after 48-72 H (hour), receptor proteins were expressed on membrane in large amount. After the cells were centrifuged at 1000 rpm for 5 min, the supernatant was discarded, and the cell pellet was collected and stored in a −20° C. fridge for reservation. It was re-suspended with Tris-Cl (pH 7.4) in the assay.

Materials for the Assay

D$_3$ receptor isotope ligand [3H]-Spiperone was purchased from AmersHam Company; (+)Butaclamol was purchased from RBI Company; GF/C glass fiber filter paper was purchased from Whatman Company; lipid-soluble scintillation solution. Tris was divided into aliquots by Genetimes Technology Inc.

Procedures

Competitive binding test for receptors: 20 µl of each of the test compounds and 20 µl of the radioactive ligand together with 160 µl of the receptor proteins were added into the reaction tubes, and the final concentrations of the test compound and the positive drug were all 10 µmol/L. After 50 min of incubation in 30° C. water bath, the tubes were immediately moved to ice bath to terminate the reactions. GF/C glass fiber filter papers were used for rapid sucking filtration on a Millipore cell sample collector, elution buffer (50 mM Tris-HCl, PH 7.4) was applied for 3 ml×3 times, and microwave was applied for 4-5 min for drying. The filter papers were moved into 0.5 ml centrifuge tubes, and 500 µl of lipid-soluble scintillation solution was added. The tubes were allowed to stand still for over 30 min in dark, and the intensities of radioactivity were measured by a counter. The percentage inhibition rates of each compound against the binding of isotope ligands were calculated according to the following formula:

Inhibition rate(I%)=[(Total binding tube cpm−compound cpm)/(Total binding tube cpm−non-specific binding tube cpm)]×100%

The results are listed in Table 1.

Example 21

5HT$_{2E}$ Receptor Binding Assay

Preparation of Membrane

Rats were sacrificed by cervical dislocation on ice. Brain mantle was rapidly taken, and 2 brain mantles were combined into a centrifuge tube, to which 3 ml of buffer (0.05 M Tris-HCl buffer, 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation at 37° C. was conducted for 10 min, the weight of the tubes were adjusted using a balance after the incubation. Centrifugation was conducted at 12000 r, 4° C. for 20 min, the supernatant was discarded, and 3 ml of buffer was added (0.05M Tris-HCl buffer: 6.05 g of Tris was dissolved in 1000 ml of double-distilled water, and concentrated HCl was used to adjust to pH 7.5). Vortex mixer was used for blending, and then 5 ml of buffer was added. Centrifugation was conducted (repeated 3 times). After the centrifugations, the supernatant was discarded, and the pellets were stored at −80° C. for future use.

Materials for the Receptor Binding Assay

Isotope ligand [$^3$H]-mesulergine (67.0 Ci/mmol) was purchased from PerkinElmer Company; mianserin was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of buffer (0.05 M Tris-HCl buffer: 6.05 g of Tris was dissolved in 1000 ml of double-distilled water, and concentrated HCl was used to adjust to pH 7.5), and homogenizer was used for evenly dispersing. 15 tubes were mixed into a 100 ml container, and appropriate amount of homogenized liquid was added to give 50 ml of membrane suspension, which was reserved for future use.

(2) 100 µL of membrane preparation and 100 µL of buffer (0.05 M Tris-HCl buffer: 6.05 g of Tris was dissolved in 1000 ml of double-distilled water, and concentrated HCl was used to adjust to pH 7.5) were added into each reaction tube.

(3) 100 µL of homogenized liquid was added into the total binding tube (TB), 100 µL of Methysergide (final concentration $10^{-5}$ M (mole/liter)) was added into the non-specific binding tube (NB), and 100 µL of the test compound (final concentration $10^{-5}$ M) was added into the specific binding tube (SB) for each compound.

(4) 10 µL of radioactive ligand [$^3$H]-mesulergine was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate($I$%)=[(Total binding tube cpm−compound cpm)/(Total binding tube cpm−non-specific binding tube cpm)]×100%

Each assay for the compounds was conducted in duplicate. The results are listed in Table 1.

The results of in vitro assay indicated that, compounds 11, 12, 17, 18 and 32 have relatively stronger affinities to four receptors ($D_2$, $D_3$, $5-HT_{1A}$ and $5-HT_{2A}$). In particular, compounds 11 and 12 were equivalent to aripiprazole.

Example 22

MK-801 Induced High Activity—The In Vivo Anti-Schizophrenia Activity of the Compounds Animals and Reagents Healthy mice of Kunming breed (with half male and half female, (20±2) g) were provided by Qinglongshan Animal Cultivation Center, Nanjing.

Ascorbic acid was provided by Sinopharm Chemical Reagent Co. Ltd.

MK-801 was produced by Sigma Company, USA; the formulation method: 0.1% vitamin C was used to formulate a 1 mg/ml solution.

Test positive drugs: haloperidol, clozapine, risperidone, olanzapine, aripiprazole, ziprasidone, quetiapine.

Tween 80, with the concentration of 10%.

Procedures

Mice with qualified body weight were selected, and randomly divided into blank group, model group, positive control group (risperidone group) and drug group. 10% Tween was administered intragastrically to the blank group and the model group at 0.1 ml/10 g; risperidone was administered intragastrically to the positive control group at 0.1 mg/kg; and corresponding amounts of drugs were administered intragastrically to the drug groups, respectively. 1 H after the administration, 0.1% of ascorbic acid was intraperitoneally injected to the blank group at 0.1 ml/10 g; and the model group, the positive control group (30 min) and the drug group were intraperitoneally injected the MK-801 solution at 0.1 mg/kg. Subsequently, the spontaneous activities of the mice of each group in 90 min were measured. The results are listed in Table 3.

The results of this assay indicate that, when compared to the model group, risperidone, compound 4, 6 and 12 can not only significantly improve the MK-801 induced high activity, but also effectively improve the apomorphine induced clambering symptoms, and they did not cause EPS at effective dosage, indicating that they have notable anti-schizophrenia effects.

Example 23

Apomorphine Induced Clambering Assay of Mice

Animals

Healthy KM mice (male, with body weight of 18-22 g) were provided by Qinglongshan Animal Cultivation Center, Nanjing.

Main Reagents

Test positive drugs: haloperidol, clozapine, risperidone, olanzapine, aripiprazole, ziprasidone, quetiapine.

Apomorphine provided by Sigma Company was dissolved in 0.9% NaCl (containing 0.1% vitamin C) before use, and was freshly formulated before use.

Vitamin C, F20061113, was provided by Sinopharm Chemical Reagent Co. Ltd.

Sodium chloride injection, H32026305, was provided by Xuzhou No. 5 Pharmaceutical Factory Co. Ltd.

Instruments: self-made clambering cage, chronograph.

Procedures: apomorphine induced clambering assay of mice KM mice (male, with body weight of 18-22 g) were randomly divided into negative control group, model group, positive drug groups for each dosage (risperidone, aripiprazole, ziprasidone, quetiapine, olanzapine, haloperidol, clozapine), and compound groups for each dosage (the specific dosages are listed in Table 2 below), with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. 1 H after the intragastric administration, apomorphine was subcutaneously injected (1 mg/kg), with the volume as 0.1 ml/10 g. After the injection of apomorphine, the mice were immediately put into the clambering cages. After 5 min of adaptation, the behaviors of the mice at 10-11, 20-21, 30-31 min after the injection of apomorphine were observed. The total clambering distances were significantly reduced, which are significant in statistics when compared to the blank control group and the model group (P<0.01). The results are listed in Table 2 below.

Example 24

Catalepsy Assay

Animals

Healthy mice of Kunming breed (with half male and half female, (22±2) g) were provided by Qinglongshan Animal Cultivation Center, Nanjing.

Main reagents: the test drugs, haloperidol, clozapine, risperidone, olanzapine, aripiprazole, ziprasidone.

Instruments: self-made bar-grabbing apparatus: stainless steel bar in mice box, which was 0.3 cm in diameter and 5 cm above the bench.

Procedures

KM mice (half male and half female, with body weight of 20-24 g) were randomly divided into negative control group, model group, positive drug groups for each dosage (risperidone, aripiprazole, ziprasidone, quetiapine, olanzapine, haloperidol, clozapine), and compound groups for each dosage, with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. At 30 min, 60 min, 90 min after the intragastric administration, the two forepaws of the mice were gently placed on the bars (which were 20 cm in length, 0.3 cm in diameter, and 5.5 cm above the bench), and the hindpaws of the animals were placed on the bottom of the box. The durations for the mice to maintain the posture with the two forepaws on the bars were recorded, and 30 s of spasticity without moving was considered as the positive response. In the case the forepaws of the mice were not put down persistently, the observation was terminated at 60 s. The numbers of animals with positive response in each of the compound dosage groups were counted.

The results are listed in Table 3.

Example 25

Acute Toxicity Study

Limit Test of Sequential Assay

KM mice (half male and half female) were randomly divided into several groups (with 2-5 mice in each group), which were respectively the 2000 mg/kg groups for each compound, and the solvent group. 0.2 ml/10 g were administered intragastrically. The death of the animals in 3 days were observed. (In the case 3 or more animals survived in 3 days without notable abnormity in their life states, the observation was continued until the assay was completed in 7 days. In the case 3 or more animals died in 3 days, the median lethal dose method was used to determine the $LD_{50}$).

Pre-Assay for the Median Lethal Dose Method

KM mice (half male and half female) were randomly divided into several groups (with 4 mice in each group), which were respectively the 1500 mg/kg, 1000 mg/kg, 500 mg/kg groups for each compound, and the solvent group. 0.2 ml/10 g were administered intragastrically, and the death of the animals in 1-3 days were observed.

Results

The $LD_{50}$ of single intragastric administration in mice was higher than 2000 mg/kg, which was comparable to aripiprazole (1400 mg/kg) and ziprasidone (2000 mg/kg), showing far lower toxicity than risperidone (82.1 mg/kg). These results indicated a relatively low acute toxicity.

TABLE 1

Inhibition % or $IC_{50}$ of the compounds for each receptor

| No. | Compound Structure | $D_2$ Inhibition % | $5HT_{1A}$ Inhibition % or ($IC_{50}$, nM) | $5HT_{2A}$ Inhibition % or ($IC_{50}$, nM) | $D_3$ Inhibition % | $5HT_{2C}$ Inhibition % |
|---|---|---|---|---|---|---|
| 1 | 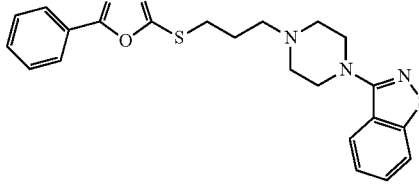 | 62.4% | 17.9% | 87.1% | — | — |
| 2 | 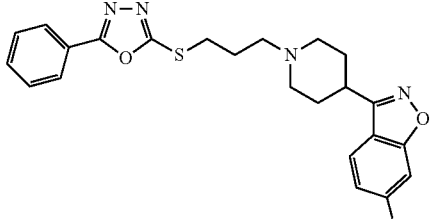 | 77.5% | 6.1% | 11.0% | — | — |
| 3 | 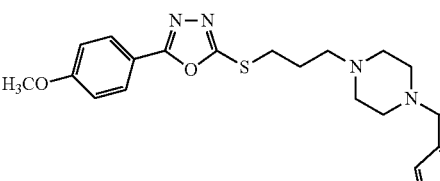 | 108.4% | 8.82$^a$ | 2.27$^a$ | 99.5% | 98.5% |
| 4 | 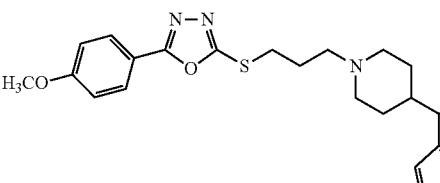 | 112.6% | 12.7$^a$ | 0.51$^a$ | 101.1% | 82.1% |

TABLE 1-continued

Inhibition % or IC$_{50}$ of the compounds for each receptor

| No. | Compound Structure | D$_2$ Inhibition % | 5HT$_{1A}$ Inhibition % or (IC$_{50}$, nM) | 5HT$_{2A}$ Inhibition % or (IC$_{50}$, nM) | D$_3$ Inhibition % | 5HT$_{2C}$ Inhibition % |
|---|---|---|---|---|---|---|
| 5 | 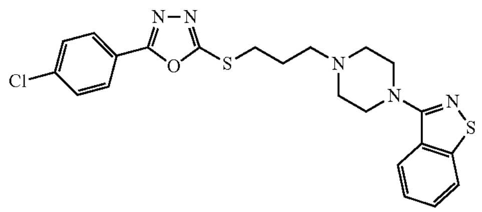 [SMILES: Clc1ccc(-c2nnc(SCCCN3CCN(c4nsc5ccccc45)CC3)o2)cc1] | 92.7% | 26.9$^a$ | 62.5$^a$ | 98.7% | 56.5% |
| 6 | 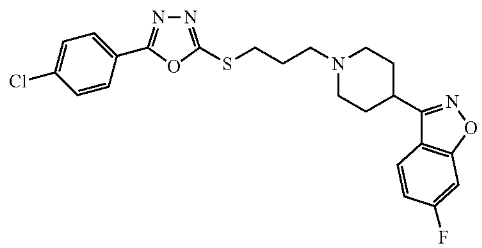 [SMILES: Fc1ccc2c(C3CCN(CCCSc4nnc(-c5ccc(Cl)cc5)o4)CC3)noc2c1] | 103.7% | 19.9$^a$ | 15.1$^a$ | 101.3% | 68.1% |
| 7 | 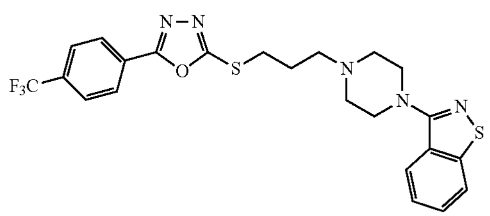 [SMILES: FC(F)(F)c1ccc(-c2nnc(SCCCN3CCN(c4nsc5ccccc45)CC3)o2)cc1] | 80.6% | 112.8% | 98.8% | — | — |
| 8 | 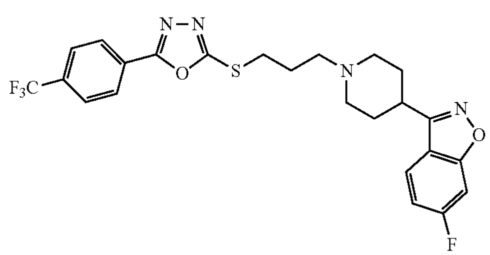 [SMILES: Fc1ccc2c(C3CCN(CCCSc4nnc(-c5ccc(C(F)(F)F)cc5)o4)CC3)noc2c1] | 105.2% | 20.8% | 100.9% | — | — |
| 9 | 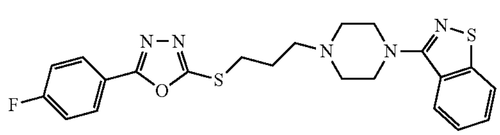 [SMILES: Fc1ccc(-c2nnc(SCCCN3CCN(c4nsc5ccccc45)CC3)o2)cc1] | 84.8% | 106.6% | 103.3% | — | — |
| 10 | 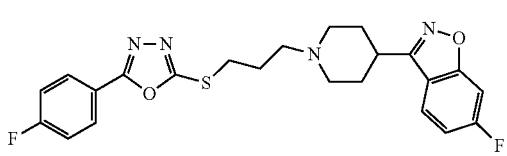 [SMILES: Fc1ccc(-c2nnc(SCCCN3CCC(c4noc5cc(F)ccc45)CC3)o2)cc1] | 88.6% | 56.4% | 117.3% | — | — |
| 11 | 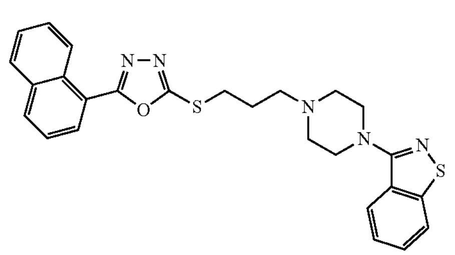 [SMILES: c1ccc2c(-c3nnc(SCCCN4CCN(c5nsc6ccccc56)CC4)o3)cccc2c1] | 25.7% | 45.8% | 91.0% | — | — |

TABLE 1-continued

Inhibition % or IC$_{50}$ of the compounds for each receptor

| No. | Compound Structure | D$_2$ Inhibition % | 5HT$_{1A}$ Inhibition % or (IC$_{50}$, nM) | 5HT$_{2A}$ Inhibition % or (IC$_{50}$, nM) | D$_3$ Inhibition % | 5HT$_{2C}$ Inhibition % |
|---|---|---|---|---|---|---|
| 12 | 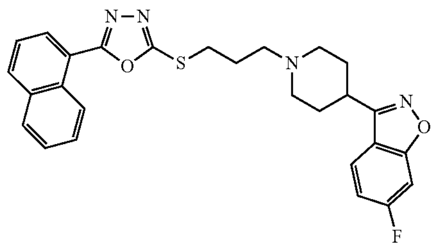 [SMILES: Fc1ccc2c(C3CCN(CCCSc4nnc(-c5cccc6ccccc56)o4)CC3)noc2c1] | 98.4% | 175$^a$ | 122.2$^a$ | 100.4% | 60.6% |
| 13 | 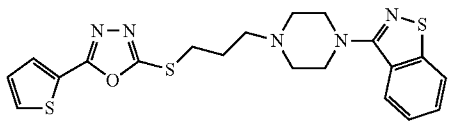 [SMILES: c1csc(-c2nnc(SCCCN3CCN(c4nsc5ccccc45)CC3)o2)c1] | 47.8% | 95.9% | 100.9% | — | — |
| 14 | 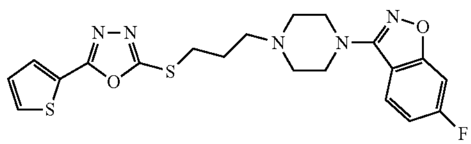 [SMILES: Fc1ccc2c(N3CCN(CCCSc4nnc(-c5cccs5)o4)CC3)noc2c1] | 110.7% | 89.7% | 101.9% | — | — |
| 15 | 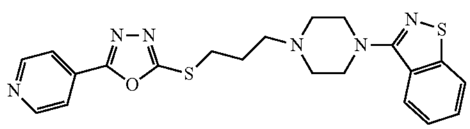 [SMILES: c1ccc2c(N3CCN(CCCSc4nnc(-c5ccncc5)o4)CC3)nsc2c1] | 88.1% | 114.3% | 95.1% | — | — |
| 16 | 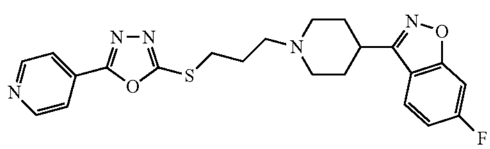 [SMILES: Fc1ccc2c(C3CCN(CCCSc4nnc(-c5ccncc5)o4)CC3)noc2c1] | 45.9% | 86.7% | 107.0% | — | — |
| aripiprazole | | 94.9% | 3.35$^a$ | 11.51$^a$ | 99.50% | 99.8% |

Note:
$^a$represents IC$_{50}$ value.

TABLE 2

Influence of the compounds on the moving distance of MK-801 high activity mice within 90 min

| Compound | Dosage (mg/kg) | Total moving distance (cm) |
|---|---|---|
| Model Group | — | 25445.72 ± 6888.12$^\#$ |
| Blank Group | — | 9221.86 ± 5118.11 |
| Compound 6 | 30 | 8454.72 ± 7864.50** |
| | 20 | 6741.35 ± 2251.52** |
| | 10 | 12997.51 ± 7859.06** |
| | 5 | 15745.74 ± 5475.41** |
| | 3 | 20912.66 ± 9887.01 |
| Compound 4 | 100 | 6954.61 ± 4931.26** |
| | 30 | 7773.56 ± 3681.67** |
| | 10 | 13574.51 ± 5340.38** |
| | 5 | 22872.82 ± 10538.51 |
| | 3 | 24988.83 ± 7617.21 |
| Compound 12 | 100 | 5665.86 ± 1799.20** |
| | 50 | 10298.82 ± 4269.95** |
| | 30 | 16163.49 ± 7769.48* |
| | 20 | 12936.50 ± 3627.24** |
| | 10 | 20521.27 ± 7898.02 |

Note:
**$p < 0.01$,
*$p < 0.05$ compared to model group;
$^\#p < 0.01$ compared to blank group

TABLE 3

Results of the in vivo animal model of the preferable compounds

| Compound No. | LD$_{50}$ (po, mg/kg) | MK-801 induced high activity (ED$_{50}$, po, mg/kg) | apomorphine induced clambering (ED$_{50}$, po, mg/kg) | catalepsy (ED$_{50}$, po, mg/kg) | catalepsy/ MK-801 | catalepsy/apomorphine |
|---|---|---|---|---|---|---|
| 4 | >2000 | 15.41 | 1.62 | 640.38 | 41.56 | 395.30 |
| 6 | >2000 | 3.31 | 4.1 | 92.73 | 28.02 | 22.62 |
| 12 | >2000 | 15.00 | 4.03 | 300.00 | 20.00 | 74.44 |
| risperidone | 82.1 | 0.01 | 0.02 | 0.3 | 15 | 30 |

Formulation Examples

The typical Examples of the formulations according to the invention are as follows.

1. Tablet

| | |
|---|---|
| Compound 4 | 5-50 mg |
| dicalcium phosphate | 20 mg |
| lactose | 30 mg |
| magnesium stearate | 5 mg |
| starch | made up to 200 mg |

In this Example, compound 4 may be replaced by equivalent amount of any compound according to the invention, especially any exemplary compounds in an equivalent amount.

2. Suspension

The aqueous suspension for oral administration was prepared, 1 ml of which contains 1-5 mg of the compound of any one of said Examples, 50 mg of sodium carboxymethyl cellulose, 1 mg of sodium benzoate, 500 mg of sorbitol and water (made up to 1 ml).

3. Injection

The parenteral composition was prepared by placing 1.5 wt % of the active ingredient of the invention in 10% (by volume) propylene glycol and water with stirring.

4. Suppository

The mixture containing 20 mg of the active ingredient of formula (I) was melt with 100 g of soybean lecithin and 1400 g of cocoa butter, and then poured into a mould and was allowed to be cooled. Each suppository contains 20 mg of active ingredient.

It is understood that the reasonable modifications will not departure from the scope of the invention. It is obvious to a person skilled in the art that the modifications in many aspects can be made to the present invention.

What is claimed:

1. A compound having the general formula (I) or a pharmaceutically acceptable salt thereof,

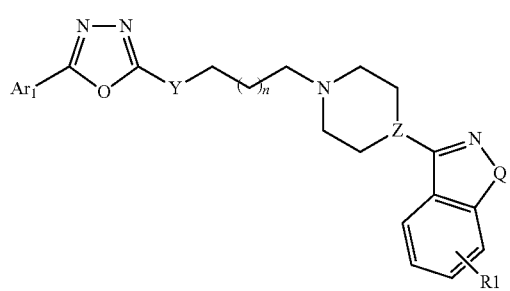

(I)

wherein,
Q is O, S or N;
Y is O or S;
Z is N or CH;
n is 1, 2 or 3;
R1 is H, halogen, cyano, C$_{1-5}$alkoxy, C$_{1-5}$alkyl, said C$_{1-5}$alkyl being unsubstituted or substituted by one or more substituents selected from the group consisting of amino, hydroxyl and halogen;
Ar$_1$ is the group of formula (II), formula (III) or formula (IV)

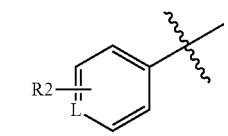

(II)

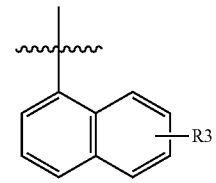

(III)

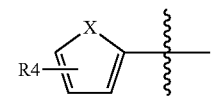

(IV)

L is CH or N;
X is O, NH, S or CH$_2$;
R2, R3 and R4 are each independently H, halogen, cyano, hydroxyl, C$_{1-5}$alkoxy, C$_{1-5}$alkyl, said C$_{1-5}$alkyl being unsubstituted or substituted by one or more substituents selected from the group consisting of amino, hydroxyl and halogen.

2. The compound according to claim 1, wherein R1, R2, R3 and R4 are each independently H, halogen, C$_{1-5}$alkoxy, C$_{1-5}$alkyl or fluorinated C$_{1-5}$alkyl.

3. The compound according to claim 2, wherein R1 is H or halogen; R2, R3 or R4 are each independently H, methoxy, Cl, F or trifluoromethyl.

4. The compound according to claim 1 or the pharmaceutically acceptable salt thereof, wherein Q is O or S.

5. The compound according to claim 1 or the pharmaceutically acceptable salt thereof, wherein Y is S.

6. The compound according to claim 1 or the pharmaceutically acceptable salt thereof, wherein n is 1.

7. The compound according to claim 1 or the pharmaceutically acceptable salt thereof, wherein X is S.

8. The compound according to claim 1 or the pharmaceutically acceptable salt thereof, wherein Ar$_1$ is the group of formula (II), Q is O or S; Y is S; Z is N or CH; n is 1; L is CH or N; and R1 and R2 are each independently H, methoxy, Cl, F or trifluoromethyl.

9. The compound according to claim 1 or the pharmaceutically acceptable salt thereof, wherein $Ar_1$ is the group of formula (III), Q is O or S; Y is S; Z is N or CH; n is 1; and R1 and R3 are each independently H or F.

10. The compound according to claim 1 or the pharmaceutically acceptable salt thereof, wherein $Ar_1$ is the group of formula (IV), Q is O or S; Y is S; Z is N or CH; n is 1; and R1 and R4 are each independently H or F.

11. The compound according to claim 1 or the pharmaceutically acceptable salt thereof, wherein Q is O, and Z is CH.

12. The compound according to claim 1 or the pharmaceutically acceptable salt thereof, wherein Q is S, and Z is N.

13. The compound according to claim 1 or the pharmaceutically acceptable salt thereof, wherein the compound is selected from the group consisting of:
- 2-((3-(4-(3-benzisothiazole)-1-piperazinyl)propylthio)-5-phenyl-1,3,4-oxadiazole;
- 2-((3-(4-(3-(6-fluoro-benzisoxazole))-1-piperidyl)propylthio)-5-phenyl-1,3,4-oxadiazole;
- 2-((3-(4-(3-benzisothiazole)-1-piperazinyl)propylthio)-5-(4-methoxyphenyl)-1,3,4-oxadiazole;
- 2-((3-(4-(3-(6-fluoro-benzisoxazole))-1-piperidyl)propylthio)-5-(4-methoxyphenyl)-1,3,4-oxadiazole;
- 2-((3-(4-(3-benzisothiazole)-1-piperazinyl)propylthio)-5-(4-chlorophenyl)-1,3,4-oxadiazole;
- 2-((3-(4-(3-(6-fluoro-benzisoxazole))-1-piperidyl)propylthio)-5-(4-chlorophenyl)-1,3,4-oxadiazole;
- 2-((3-(4-(3-benzisothiazole)-1-piperazinyl)propylthio)-5-(4-trifluoromethyl)phenyl)-1,3,4-oxadiazole;
- 2-((3-(4-(3-(6-fluoro-benzisoxazole))-1-piperidyl)propylthio)-5-(4-trifluoromethyl)phenyl)-1,3,4-oxadiazole;
- 2-((3-(4-(3-benzisothiazole)-1-piperazinyl)propylthio)-5-(4-fluoro)phenyl)-1,3,4-oxadiazole;
- 2-((3-(4-(3-(6-fluoro-benzisoxazole))-1-piperidyl)propylthio)-5-(4-fluoro)phenyl)-1,3,4-oxadiazole;
- 2-((3-(4-(3-benzisothiazole)-1-piperazinyl)propylthio)-5-(1-naphthyl)-1,3,4-oxadiazole;
- 2-((3-(4-(3-(6-fluoro-benzisoxazole))-1-piperidyl)propylthio)-5-(1-naphthyl)-1,3,4-oxadiazole;
- 2-((3-(4-(3-benzisothiazole)-1-piperazinyl)propylthio)-5-(2-thienyl)-1,3,4-oxadiazole;
- 2-((3-(4-(3-(6-fluoro-benzisoxazole))-1-piperidyl)propylthio)-5-(2-thienyl)-1,3,4-oxadiazole;
- 2-((3-(4-(3-benzisothiazole)-1-piperazinyl)propylthio)-5-(4-pyridyl)-1,3,4-oxadiazole;
- 2-((3-(4-(3-(6-fluoro-benzisoxazole))-1-piperidyl)propylthio)-5-(4-pyridyl)-1,3,4-oxadiazole;

and their pharmaceutically acceptable salts.

14. A pharmaceutical composition, comprising the compound having formula (I) according to claim 1 or the pharmaceutically acceptable salt thereof, and pharmaceutically acceptable adjuvant.

15. A method for treating schizophrenia, comprising administrating the compound according to claim 1 or the pharmaceutically acceptable salt thereof to a patient in need thereof.

* * * * *